United States Patent
Jain et al.

(10) Patent No.: US 12,043,595 B2
(45) Date of Patent: Jul. 23, 2024

(54) LIGHT ASSISTED, CATALYST-FREE OXIDATION OF ALDEHYDES TO CARBOXYLIC ACIDS USING CARBON DIOXIDE

(71) Applicant: Council of Scientific & Industrial Research, New Delhi (IN)

(72) Inventors: Suman Lata Jain, Dehradun (IN); Shafuir Rehman Khan, Dehradun (IN); Vineet Aniya, Hyderabad (IN); Alka Kumari, Hyderabad (IN); Sandhya Saini, Dehradun (IN); Praveen Kumar Khatri, Dehradun (IN); Anjan Ray, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 189 days.

(21) Appl. No.: 17/886,023

(22) Filed: Aug. 11, 2022

(65) Prior Publication Data
US 2023/0065184 A1     Mar. 2, 2023

(30) Foreign Application Priority Data
Aug. 13, 2021   (IN) .............. 202111036982

(51) Int. Cl.
C07C 51/15   (2006.01)
C07C 51/47   (2006.01)

(52) U.S. Cl.
CPC .............. *C07C 51/15* (2013.01); *C07C 51/47* (2013.01)

(58) Field of Classification Search
CPC ....... C07C 51/15; C07C 51/47; C07C 201/12; C07D 307/68; C07D 333/40
See application file for complete search history.

(56) References Cited

PUBLICATIONS

Liuqun Gu, et al., "Unexpected CO2 Splitting Reactions to Form CO with N-Heterocyclic Carbenes as Organocatalysts and Aromatic Aldehydes as Oxygen Acceptors", Institute of Bioengineering and Nanotechnology, 31 Biopolis Way, The Nanos, Singapore 138669, J. Am. Chem. Soc. 2010, 132, 914-915.

Mjay Nair, et al., "NHC Catalyzed Transformation of Aromatic Aldehydes to Acids by Carbon Dioxide: An Unexpected Reactiont", Organic Chemistry Section, National Institute for Interdisciplinary Science and Technology (CSIR), Trivandrum 695 019, India, May 6, 2010, Organic Letters 2010, vol. 12, No. 11 2653-2655.

*Primary Examiner* — Deborah D Carr
(74) *Attorney, Agent, or Firm* — Dinsmore & Shohl LLP

(57) ABSTRACT

Method for visible-light driven oxidation of aldehydes to carboxylic acid using carbon dioxide ($CO_2$) as the oxidant in the absence of any catalyst are provided. In the disclosed process, aldehydes, when reacted with $CO_2$ in an organic solvent, either in a batch reactor or in a continuous flow reactor, under conditions of ambient temperature and pressure, using a readily available household LED lamp, yield corresponding carboxylic acids along with the formation of carbon monoxide (CO) in the effluent gas.

11 Claims, 1 Drawing Sheet

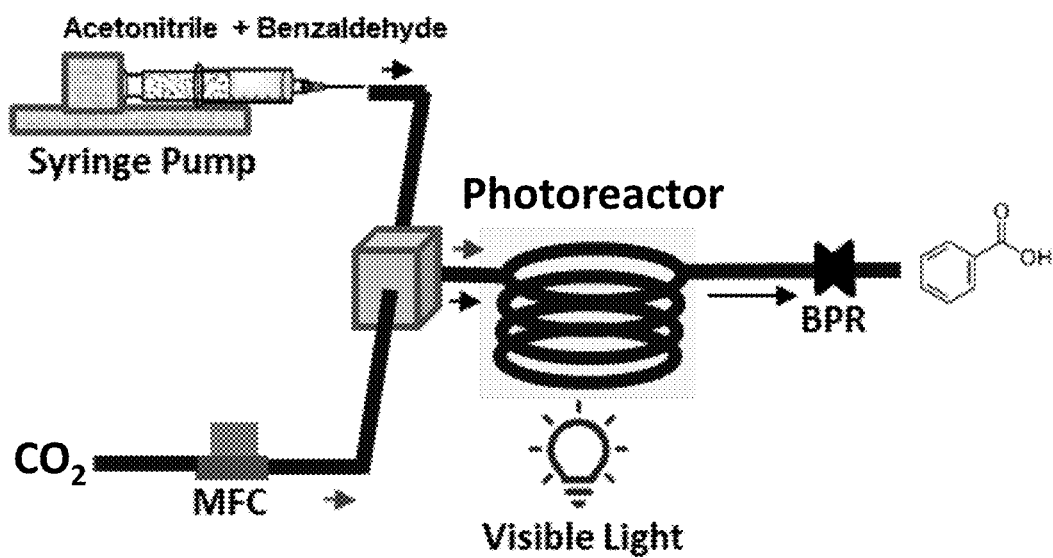

LIGHT ASSISTED, CATALYST-FREE OXIDATION OF ALDEHYDES TO CARBOXYLIC ACIDS USING CARBON DIOXIDE

CROSS-REFERENCES TO RELATED APPLICATIONS

This application claims benefit of priority under 35 U.S.C. § 119 to Indian Patent Application No. 202111036982, filed Aug. 13, 2021, which is incorporated by reference herein in its entirety.

TECHNICAL FIELD

The present disclosure relates to methods for visible-light driven catalyst-free oxidation of aldehydes to carboxylic acids using $CO_2$ as an oxidant at ambient pressure conditions.

BACKGROUND

Carbon dioxide ($CO_2$) concentration is continuously increasing in the earth's atmosphere, attributed mainly from industrialization and excessive consumption of fossil fuels. Such atmospheric $CO_2$ increase is a major cause of climate change and is accompanied by global warming.

Among the various options known for carbon dioxide mitigation, chemical fixation of $CO_2$ to produce valuable chemicals has found considerable interest in recent years (Anwar et al. J. Environ. Management, 2020, 260, 110059; Yang and Lee, Chem. Sci. 2019, 10, 3905). However, owing to the higher thermodynamic and kinetic stability, a significant amount of energy is required for the activation and conversion of $CO_2$ into value-added products. In thermal catalysis, the requirements of significantly elevated temperatures for $CO_2$ activation make these processes highly energy intensive and lead to catalyst deactivation as a result of coke formation typical of high temperature processes.

In contrast to the thermal catalysis, single-electron reduction of $CO_2$ to radical anions assisted by light, which is cheap, clean, and inexhaustible, is desirable because it is simple, sustainable, and uses mild operating conditions. So far, an extensive amount of work has been done for $CO_2$ photoreduction using different photocatalysts including semiconductors, molecular complexes and composite materials for the production of chemicals such as carbon monoxide (CO), methane ($CH_4$), and methanol ($CH_3OH$), for example.

On the other hand, the use of $CO_2$ as an oxidant is rarely reported in the literature. In open literature (Zhang et al J. Am. Chem. Soc. 2010, 132, 3, 914-915; Menon et al., Org. Lett. 2010, 12, 2653-2655), there are reports of the oxidation of aldehydes to corresponding acids using $CO_2$ as an oxidant in the presence of DBU as a base and N-heterocyclic carbenes (NHCs) as catalysts at room temperature. The use of homogeneous additional base and organocatalyst limit the practical applicability of this developed process.

Oxidation of aldehydes to carboxylic acids is one of the important transformations, as carboxylic acids and their derivatives are important synthetic intermediates for the fine chemicals, pharmaceuticals, and functional materials industries. A number of methods using stoichiometric inorganic or organic oxidants have been developed for oxidizing aldehydes to carboxylic acids; however, generation of copious amounts of hazardous waste limited their practical applicability. Subsequently, a number of catalytic methods using environment-friendly oxidant, molecular oxygen have been developed (Choudhary et al., (2011) Catal. Commun. (13), 82-86. Vanoye et al. (2013) Org. Lett. (15), 5978-5981; Shinji et al. (2016) Chem. Lett. (45), 188-190; Peixoto et al. (2017) J. Org. Chem. (82) 6232-6241). Recently, the base-promoted oxidation of aldehydes using transition metals such as (Rh, Ag, Cu, and Fe) with molecular oxygen as oxidant have been reported (Wang et al (2016) Green Chem.(18) 4605-4610. Although these strategies represent a considerable advancement, the expensive nature and multi step synthesis of metal catalysts along with the use of base and oxygen as oxidant leads to economical and environmental issues. Therefore, development of simple, environmentally benign, catalyst-free synthesis of carboxylic acids using abundant, inexpensive $CO_2$ as oxidant is highly desired.

SUMMARY

Accordingly, disclosed herein are light assisted, catalyst-free photochemical processes for the oxidation of aldehydes using carbon dioxide. The processes include oxidizing the aldehyde with $CO_2$ dissolved in a solvent under the light irradiation either in a batch or continuous flow photoreactor at a temperature from 20° C. to 40° C. and a pressure from 1 bar to 5 bar for 1 hour to 24 hours irradiation time in the batch and continuous flow photo-reactor, followed by purification, to give a corresponding carboxylic acid with the formation of carbon monoxide as a co-product in the gaseous phase.

In an embodiment, the aldehyde is selected from aromatic aldehydes substituted by electron donating or electron deficient group or is selected from aliphatic aldehydes.

In another embodiment, the aldehyde is selected from aryl aldehydes of Formula (I):

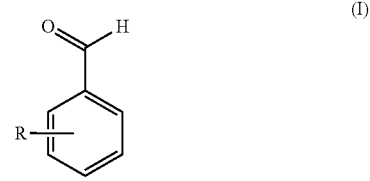

In formula (I), R is selected from the group consisting of hydrogen, halogen, methyl, ethyl, propyl, butyl, amyl, iso-propyl, isobutyl, phenyl, tolyl, biphenyl, benzyl, or naphthyl.

In yet another embodiment, the light irradiation is done by using light source having wavelength λ greater than 420 nm, preferably using a household LED light of 10 W to 50 W power.

In another embodiment, the solvent is selected from the group consisting of water, acetonitrile (ACN) or dimethylformamide (DMF) or dimethylsulfoxide (DMSO) or tetrahydrofuran (THF), or mixtures thereof as may be appropriate, in particular pure acetonitrile.

In yet another embodiment, the reaction time is preferably from 1 hour to 15 hours.

In yet another embodiment, the reaction is effective at ambient temperature (25° C.) and at 1 atmospheric pressure of $CO_2$.

In yet another embodiment, purification is carried out by column chromatography using silica gel bed.

In yet another embodiment, the yield of the product is from 30% to 98% determined on the basis of isolated carboxylic acid or based on the recovered aldehyde substrate.

Yet another embodiment provides a catalyst-free photochemical activation of $CO_2$ and its use as an oxygen transfer agent along with the production of CO as a by-product under ambient temperature and pressure (1 atm) conditions.

Yet another embodiment provides an innovative, facile, catalyst-free, economically viable and environmentally friendly synthesis of carboxylic acids from oxidation of aldehydes using $CO_2$ as an oxidant.

Yet another embodiment provides a catalyst-free photochemical route for the oxidation of aldehydes with $CO_2$ at atmospheric pressure of $CO_2$ in typically ambient temperature ranges of 15° C. to 50° C., preferably at about 25° C.

Yet another embodiment provides a catalyst-free photochemical route for the oxidation of aldehydes using $CO_2$ as oxidant in a continuous flow reactor with the yield of carboxylic acid from 20% to 80%.

Yet another embodiment provides a catalyst-free photochemical reduction of $CO_2$ to CO along with the simultaneous oxidation of aldehydes.

In another embodiment, the formation of CO in the gaseous effluent is determined by refinery gas analyzer (RGA) technique.

In another embodiment, the oxidation of aldehydes by $CO_2$ to produce carboxylic acids is amenable to a continuous process.

BRIEF DESCRIPTION OF THE DRAWING

The FIGURE is a schematic of a reactor set-up for a continuous flow process.

DETAILED DESCRIPTION

Embodiments herein provide a catalyst-free process for the oxidation of aldehydes to carboxylic acids using $CO_2$ as oxidant under mild reaction conditions.

Embodiments herein provide a method for the catalyst-free photochemical activation of $CO_2$ to provide necessary oxygen for the oxidation along with the production of carbon monoxide as a by-product.

Embodiments herein provide a catalyst-free photochemical route for the preparation of carboxylic acids using $CO_2$ as oxidant.

Embodiments herein provide to a catalyst-free photochemical route for the oxidation of aldehydes using $CO_2$ as oxidant with the conversion from 30% to 99%.

Embodiments herein provide a catalyst-free photochemical route for the oxidation of aldehydes with $CO_2$ at atmospheric pressure and ambient temperature ranges of 15° C. to 40° C., preferably at about 25° C.

Embodiments herein may include use of a polar solvent that is protic or aprotic or that is selected from water, acetonitrile or dimethylformamide or dimethylsulfoxide or tetrahydrofuran, or mixtures thereof as may be appropriate, in particular pure acetonitrile.

Embodiments herein provide a catalyst-free photochemical route for the oxidation of aldehydes to carboxylic acids in the time ranging from 1 hour to 24 hours.

Embodiments herein may include the use of a visible light source having wavelength ($\lambda$) greater than 420 nm or a broad spectrum of solar energy containing such wavelengths for the activation of the carbon dioxide under mild conditions.

Embodiments herein may include a catalyst-free photochemical route for the oxidation of aldehydes using $CO_2$ as oxidant in a continuous flow reactor with the yield of the acid being from 20% to 80%.

Embodiments herein provide a catalyst-free photochemical reduction of $CO_2$ to CO along with the simultaneous oxidation of aldehydes.

Specific embodiments of light assisted, catalyst-free photochemical process for oxidation of aldehydes using carbon dioxide will now be described. The processes may include reacting an aldehyde having a —CHO group in a polar organic solvent with carbon dioxide at temperature from 20° C. to 40° C. and at atmospheric pressure under the visible light irradiation to prepare the corresponding carboxylic acid along with the production of CO as a co-product in gaseous effluent.

As utilized herein including in the claims "oxidation of aldehyde" means insertion of an oxygen derived from the $CO_2$ into the —CHO group of the compound to convert it into —COOH.

As utilized herein including in the claims "reactants" collectively references both aldehyde and $CO_2$ (oxidant) and the "solvents" including both aqueous and organic reaction media.

Within this disclosure, "visible light" means light having a wavelength ($\lambda$) greater than 420 nm.

In embodiments, any compound having a —CHO group can be employed in the process described herein. Aromatic aldehydes—whether substituted by electron donating or electron deficient group—are preferred, but aliphatic aldehydes, either unsaturated and/or linear, can also be employed. Most of the aforementioned aldehydes are available commercially and may be used as received.

Constituents

Reactants

Embodiments herein relate to the oxidation of the aldehydes with $CO_2$ without using any catalyst under light irradiation.

The aldehyde may be any organic compound containing a —CHO group. Aromatic aldehydes, which are suitable for the processes herein, include benzaldehyde and its substituted derivatives, heterocyclic aldehydes and analogously, the cyclic, or branched or chain isomers of aliphatic aldehydes, whether saturated or unsaturated, containing 4 to 10 carbon atoms, and their substituted variants.

Oxidant (Carbon Dioxide)

In embodiments herein, carbon dioxide is used as an oxidant in place of conventional oxidants such as $O_2$ or $H_2O_2$ under visible illumination. In the reactions, of the two oxygen atoms present in carbon dioxide, one oxygen atom is converted in the oxidation of —CHO to —COOH and the other oxygen atom is converted to carbon monoxide. The reaction mixture containing substrates and solvent is either saturated with $CO_2$ or is purged continuously with $CO_2$ flow for effective oxidation.

Organic Solvents

Substrates (aldehyde and $CO_2$) used in the embodiments herein are preferably dissolved in organic solvents. Polar organic solvents may be used owing to the higher solubility of $CO_2$ in polar solvents. Suitable organic solvents include specifically, but not limited to, dimethylformamide (DMF), dimethylacetamide (DMA), acetonitrile (ACN), dimethylsulfoxide (DMSO), and N-methyl pyrolidone (NMP), or mixtures thereof.

Standard Protocol (Batch and Continuous Process)

According to embodiments, aldehyde substrate in a polar organic solvent, preferably acetonitrile (1:2 to 1:10 weight ratio with respect to the substrate) is taken into a 60-mL vessel for a batch process. The reaction mixture is saturated with $CO_2$ by purging. The reaction vessel is sealed and irradiated with 20-W LED light for 1.0 hour to 15 hours. The intensity of the LED light at the reaction flask is measured to be 80 $W/m^2$ to 100 $W/m^2$ by an intensity meter. The progress of the reaction is monitored by thin layer chromatography using silica gel. After completion of the reaction, the solvent is evaporated under reduced pressure, and the concentrated residue is subjected to column chromatography on a silica gel (100-200 mesh) column using a 9:1 hexane-ethyl acetate solvent mixture as an eluent to afford pure carboxylic acid. The yield of the acid is obtained in a range of 30% to 98%. The formation of CO in the effluent gas is confirmed by Residual Gas Analysis (RGA).

In embodiments, a continuous process may be employed. A schematic experimental setup is provided in the FIGURE and includes a continuous-flow reactor assembly that includes a syringe pump, a digital mass flow controller, and non-return valves that are connected to a T-micro mixer for efficient mixing of reactant before sending to the reaction flow line. The continuous flow reactor line is 1000 mm long with an outer diameter of 3 mm and an inner diameter of 1.5 mm that is connected to a back-pressure regulator (BPR). The reactor is illuminated with visible light of intensity 80 $W/m^2$ to 100 $W/m^2$, and the product mixture is collected at the outlet of the rector.

While the processes herein are valuable for oxidizing aldehydes in general to obtain carboxylic acids, they are particularly useful for obtaining aromatic carboxylic acids from the corresponding aryl aldehydes such as benzaldehyde, tolualdehyde, anisaldehyde, chlorobenzaldehyde, and homologues thereof, as well as heterocyclic aldehydes such as furfural and analogues thereof.

Specific examples of suitable aldehydes used in the invention are aryl aldehydes corresponding to Formula (I):

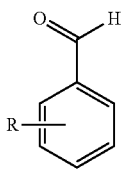

(I)

In Formula (I), R may be hydrogen, alkyl, aryl, chloro, or methoxy, for example. In specific examples, R of formula (I) may be hydrogen, halogen, methyl, ethyl, propyl, butyl, amyl, isopropyl, isobutyl, phenyl, tolyl, biphenyl, benzyl, or naphthyl, for example. Preferably, benzaldehyde and its substituted derivatives are utilized.

EXAMPLES

Following examples are given by way of illustration and therefore should not be construed to limit the scope of this disclosure or the appended claims.

Example 1

General Procedure for the Oxidation of Benzaldehyde

Benzaldehyde (1a) and polar organic solvent, preferably acetonitrile (1:2 to 1:10 weight ratio with respect to the substrate) was taken into a 60-mL vessel. The reaction mixture was saturated with $CO_2$ by purging. The reaction vessel was sealed and irradiated with 20 W LED light for 2 h. The intensity of the LED light at the reaction flask was measured to be 86 $W/m^2$ by intensity meter. The progress of the reaction was monitored by thin-layer chromatography using silica gel. After completion of the reaction, the solvent was evaporated under reduced pressure and the resulting concentrated residue was subjected to column chromatography on a silica gel (100-200 mesh) column using 9:1 hexane-ethyl acetate solvent mixture as eluent to afford pure benzoic acid as white crystals in 96% isolated yield.

Example 2

Oxidation of Benzaldehyde in Continuous Flow Reactor

Benzaldehyde (1a) was mixed with acetonitrile solvent in 1:2 to 1:5 weight ratio and pumped continuously through a syringe pump. The reactant solution was pumped at a flow rate of 72 μL/min and directed into the tubing of the reactor via T-micromixer. The $CO_2$ was introduced into the system through MFC (mass flow controller) and was mixed with the solution in the T-micromixer to form a $CO_2$-saturated reactant solution stream before sending it into a photochemical reactor. The combined flow rate was adjusted to the reactor volume of 7 mL with a residence time of 4 minutes at 20° C. A terminal BPR was connected with a 60 psi line to maintain the system pressure and prevent out-gassing. Benzoic acid product was obtained with 75% yield.

Example 3

Oxidation of Benzaldehyde in Dark

Benzaldehyde (1a) and polar organic solvent, preferably acetonitrile in (1:2 to 1:10 weight ratio with respect to the substrate) was taken into a 60-mL vessel. The reaction mixture was saturated with $CO_2$ by purging. The reaction vessel was sealed and kept in the dark for 6 hours. After completion of the reaction, the solvent was evaporated under reduced pressure, and the resulting residue was analyzed by gas chromatography with a flame-ionization detector (GC-FID) and $^1H$ NMR. There was no reaction observed, and original substrate could be recovered after the reaction. This confirmed that light irradiation is essentially required for the activation of $CO_2$ to provide necessary oxygen for the oxidation reaction.

Example 4

Oxidation of Benzaldehyde without $CO_2$

Benzaldehyde (1a) and polar organic solvent, preferably acetonitrile (1:2 to 1:10 weight ratio with respect to the substrate) was taken into a 60-mL vessel. The reaction mixture was purged with $N_2$ in place of $CO_2$. The reaction vessel was sealed and irradiated with a 20-W LED light for 6 hours. After completion of the reaction, the solvent was evaporated under reduced pressure, and the resulting residue was analyzed by GC-FID and $^1H$ NMR. There was no reaction observed, and the original substrate could be recovered after the reaction. This confirmed that the required oxygen for the oxidation of benzaldehyde was derived from carbon dioxide.

Example 5

Oxidation of Benzaldehyde Using Different Solvents

Benzaldehyde (1a) and an organic solvent (1:2 to 1:10 weight ratio with respect to the substrate) were taken into a 60-mL vessel. The reaction mixture was saturated with $CO_2$ by purging. The reaction vessel was sealed and irradiated with a 20-W LED light for 2 hours. The intensity of the LED light at the reaction flask was measured to be 86 $W/m^2$ by intensity meter. After completion of the reaction, the solvent was evaporated under reduced pressure, and the resulting residue was subjected to column chromatography on a silica gel (100-200 mesh) column using a 9:1 hexane—ethyl acetate solvent mixture as an eluent to afford pure benzoic acid. The results of the experiments in different solvents are summarized in Table 1, entries 1 and 5-9.

Example 6

Oxidation of Different Aldehydes Under Optimized Conditions

Aldehyde (1b-1h) and polar organic solvent, preferably acetonitrile (1:2 to 1:10 weight ratio with respect to the substrate) was taken into a 60-mL vessel. The reaction mixture was saturated with $CO_2$ by purging. The reaction vessel was sealed and irradiated with 20-W LED light for 2 hours to 10 hours. The intensity of the LED light at the reaction flask was measured to be 86 $W/m^2$ by intensity meter. The progress of the reaction was monitored by thin-layer chromatography using silica gel. After completion of the reaction, the solvent was evaporated under reduced pressure and the resulting residue was subjected to column chromatography on a silica gel (100 to 200 mesh) column using a 9:1 hexane—ethyl acetate solvent mixture as an eluent to afford pure acid. The isolated yields and the reaction times of these experiments are summarized in Table 1, entries 10-19.

Accordingly, embodiments herein provide a catalyst-free light assisted utilization of $CO_2$ for chemical synthesis.

Embodiments herein further provide a catalyst-free photochemical synthesis of carboxylic acids from oxidation of aldehydes using $CO_2$ as an oxidant under ambient temperature and pressure conditions. The use of $CO_2$ as an oxidant offer several advantages as it is abundantly available, safe, and inexpensive; also it provided carbon monoxide, an important building block as a co-product during the oxidation process.

Using benzaldehyde and its derivatives substituted with electron donating groups as substrates the conversion and yield of the corresponding acids remained higher than the substrates having electron withdrawing groups.

The best results were obtained in acetonitrile solvent; whereas, DMF and DMA being a $CO_2$-philic solvent showed moderate reactivity.

The processes disclosed herein provide a viable approach that can serve as a tool for chemical fixation of $CO_2$ in a sustainable way under mild operating conditions.

We claim:

1. A light assisted, catalyst-free photochemical process for oxidation of aldehydes using carbon dioxide, the process comprising:
    oxidizing an aldehyde with $CO_2$ dissolved in a solvent under light irradiation in a batch or continuous flow photoreactor at a reaction temperature from 20° C. to 40° C. and a reaction pressure from 1 bar to 5 bar for an irradiation time from 1 hour to 24 hours to obtain a carboxylic acid product with formation of gaseous carbon monoxide as a co-product; and
    purifying the carboxylic acid product.
2. The process of claim 1, wherein the aldehyde is selected from:
    aromatic aldehydes substituted with an electron donating group or an electron deficient group; or
    aliphatic aldehydes.

TABLE 1

Photochemical oxidation of aldehydes with $CO_2$

| No. | Aldehyde | Acid | React, time (h) | Solvent | Yield |
|---|---|---|---|---|---|
| 1 | Benzaldehyde (1a) | Benzoic acid (2a) | 2 | $CH_3CN$ | 96%[a] |
| 2[c] | Benzaldehyde (1a) | Benzoic acid (2a) | — | $CH_3CN$ | 75%[a] |
| 3[d] | Benzaldehyde (1a) | — | 6 | $CH_3CN$ | — |
| 4[e] | Benzaldehyde (1a) | — | 6 | $CH_3CN$ | — |
| 5 | Benzaldehyde (1a) | Benzoic acid (2a) | 2 | DMA | 78%[a] |
| 6 | Benzaldehyde (1a) | Benzoic acid (2a) | 2 | DMF | 75%[a] |
| 7 | Benzaldehyde (1a) | Benzoic acid (2a) | 2 | DMSO | (55%)[b] |
| 8 | Benzaldehyde (1a) | Benzoic acid (2a) | 2 | NMP | (20%)[b] |
| 9 | Benzaldehyde (1a) | Benzoic acid (2a) | 2 | $H_2O$ | (45%)[b] |
| 10 | 4-methylbenzaldehyde (1b) | 4-methylbenzoic acid (2b) | 4 | $CH_3CN$ | 97%[a] |
| 11 | 4-methoxybenzaldehyde (1c) | 4-methoxybenzoic acid (2c) | 6 | $CH_3CN$ | 95%[a] |
| 12 | 4-chlorobenzaldehyde (1d) | 4-chlorobenzoic acid (2d) | 10 | $CH_3CN$ | 85%[a] |
| 13 | 3,4-dichlorobenzaldehyde (1e) | 3,4-dichloro-benzoic acid (2e) | 10 | $CH_3CN$ | 72%[a] |
| 14 | 4-nitrobenzaldehyde (1f) | 4-nitrobenzoic acid (2f) | 12 | $CH_3CN$ | (30%)[b] |
| 15 | Furan-2-carboxaldehyde (1g) | Furan-2-carboxylic acid (2g) | 12 | $CH_3CN$ | (51%)[b] |
| 16 | 2-thiophene-carboxylic acid (1h) | 2-thiophene-carboxylic acid (2h) | 12 | $CH_3CN$ | (52)[b] |
| 17 | 3,4-dimethoxybenzaldehyde (1i) | 3,4-dimethoxy-benzoic acid (2i) | 10 | $CH_3CN$ | (40%)[b] |
| 18 | 2-methylbenzaldehyde (1j) | 2-methyl benzoic acid (2j) | 6 | $CH_3CN$ | (42%)[b] |
| 19 | Cinnamaldehyde (1k) | Cinnamic acid (2k) | 12 | $CH_3CN$ | (36%)[b] |

[a]Isolated yield;
[b]Yield based on recovered aldehyde;
[c]In a flow photoreactor;
[d]Under dark conditions;
[e]Without $CO_2$, under $N_2$.

3. The process of claim 1, wherein the aldehyde is an aryl aldehyde of Formula (I):

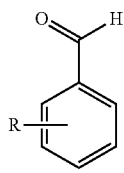 (I)

where R is selected from the group consisting of hydrogen, halogen, methyl, ethyl, propyl, butyl, amyl, isopropyl, isobutyl, phenyl, tolyl, biphenyl, benzyl, and naphthyl.

4. The process of claim 1, wherein the light irradiation comprises irradiating with a light source having a wavelength greater than 420 nm.

5. The process of claim 4, wherein the light source is a household LED light having a power from 10 W to 50 W.

6. The process of claim 1, wherein the solvent is selected from the group consisting of water, acetonitrile, dimethylformamide, dimethylsulfoxide, tetrahydrofuran, and mixtures thereof.

7. The process of claim 6, wherein the solvent comprises acetonitrile.

8. The process of claim 1, wherein the irradiation time is from 1 hour to 15 hours.

9. The process of claim 1, wherein the reaction temperature is from 25° C. to 35° C. and a pressure of $CO_2$ in the photoreactor is 1 atmosphere.

10. The process of claim 1, wherein the purifying comprises performing column chromatography on the carboxylic acid product in a silica gel bed.

11. The process of claim 1, wherein the process results in a yield of the carboxylic acid product from 30% to 97% determined on the basis of isolated carboxylic acid.

* * * * *